(12) United States Patent
Nycz et al.

(10) Patent No.: US 8,062,259 B2
(45) Date of Patent: Nov. 22, 2011

(54) CANNULATED SENSING DEVICE

(75) Inventors: Jeffrey H. Nycz, Warsaw, IN (US); Christopher Michael Lyons, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/639,368

(22) Filed: Dec. 16, 2009

(65) Prior Publication Data

US 2010/0094255 A1 Apr. 15, 2010

Related U.S. Application Data

(63) Continuation of application No. 11/482,081, filed on Jul. 6, 2006, now Pat. No. 7,666,165.

(51) Int. Cl.
*A61M 5/178* (2006.01)
*A61M 31/00* (2006.01)
*A61M 5/32* (2006.01)
*A61M 25/00* (2006.01)

(52) U.S. Cl. ............ 604/164.01; 604/65; 604/272; 604/264

(58) Field of Classification Search ............ 604/164.01, 604/890.1, 272, 264, 280, 158, 164.07, 170.01–170.02, 604/164.09
See application file for complete search history.

(56) References Cited

U.S. PATENT DOCUMENTS

| 4,173,228 | A | 11/1979 | Van Steenwyk et al. |
| 5,954,701 | A | 9/1999 | Matalon |
| 6,391,005 | B1 * | 5/2002 | Lum et al. ............ 604/117 |
| 6,719,686 | B2 | 4/2004 | Coakley et al. |
| 6,733,488 | B2 | 5/2004 | Gambale et al. |
| 2001/0007933 | A1 | 7/2001 | Lesh et al. |
| 2003/0120297 | A1 | 6/2003 | Beyerlein |
| 2006/0063126 | A1 * | 3/2006 | Aloise et al. ............ 433/81 |
| 2007/0112305 | A1 | 5/2007 | Brimhall |

FOREIGN PATENT DOCUMENTS

WO 9304728 A1 3/1993

* cited by examiner

*Primary Examiner* — Nicholas D Lucchesi
*Assistant Examiner* — Rebecca E Eisenberg

(57) ABSTRACT

A cannulated sensing device is disclosed and can include a housing that can have a proximal end and a distal end. A cannula can extend from the proximal end of the housing to the distal end of the housing. Further, a sensor can be attached to the distal end of the housing.

12 Claims, 9 Drawing Sheets

CANNULATED SENSING DEVICE

FIELD OF THE DISCLOSURE

The present disclosure relates generally to devices for treating diarthrodial joints. More specifically, the present disclosure relates to injecting a therapeutic agent into diarthrodial joints.

BACKGROUND

Hyaluronic acid is naturally found in many tissues of the body such as skin, cartilage, and the vitreous humor. Hyaluronic acid can be used to treat osteoarthritis of various diarthrodial joints, e.g., knee joints, hip joints, etc. In order to properly treat certain diarthrodial joints, e.g., hip joints, it is desirable to inject hyaluronic acid deep into a joint capsule of the diarthrodial joint—regardless of patient size. As such, it is desirable to locate synovial fluid associated with a diarthrodial joint and it is desirable to locate a tip of an injection needle prior to injection of the hyaluronic acid within a joint capsule.

Accordingly, there is a need for a device for locating synovial fluid in a patient and for locating a needle tip within a patient prior to injecting a therapeutic agent such as hyaluronic acid.

DETAILED DESCRIPTION OF THE DRAWINGS

Figure 1:
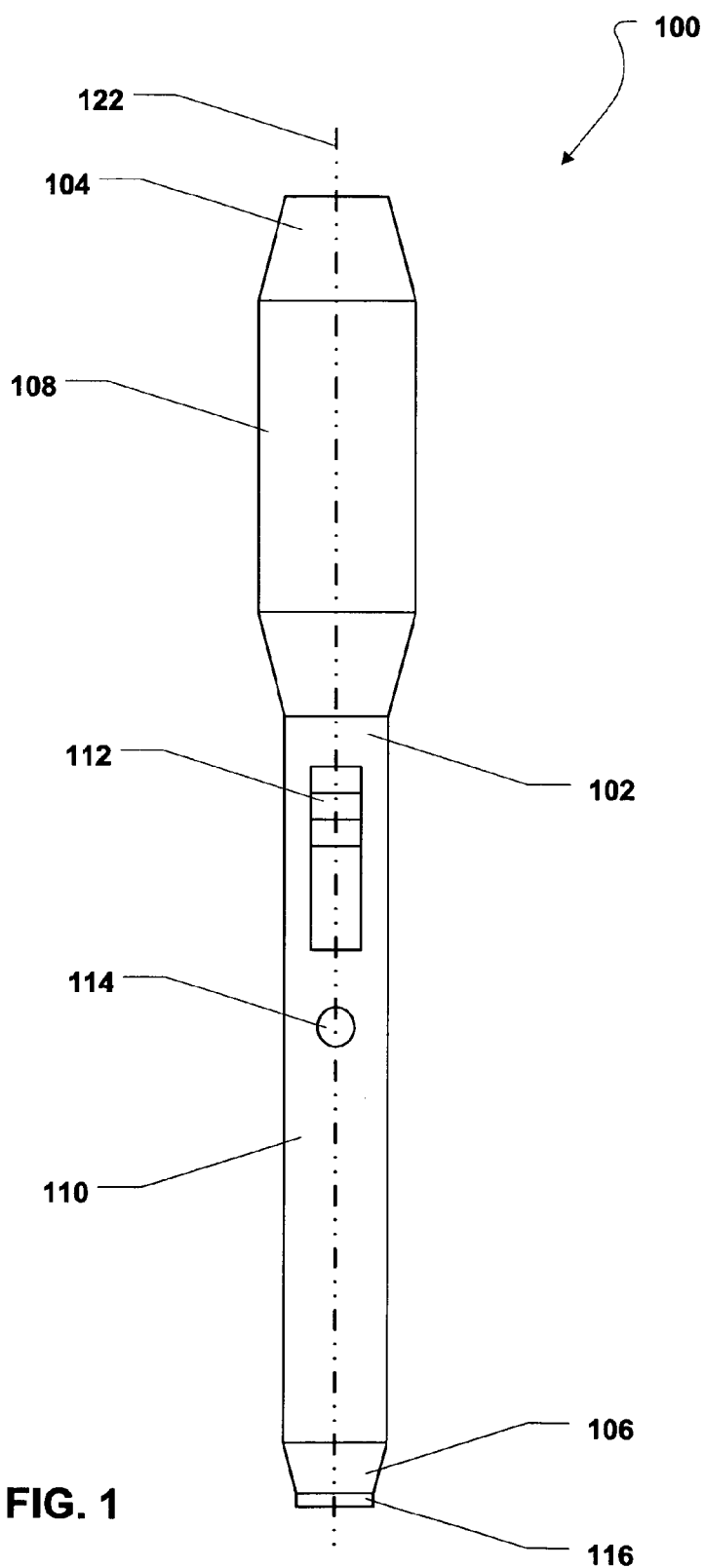
FIG. 1 is a plan view of a cannulated sensing device.

A cannulated sensing device is disclosed and can include a housing that can have a proximal end and a distal end. A cannula can extend from the proximal end of the housing to the distal end of the housing. Further, a sensor can be attached to the distal end of the housing.

In another embodiment, an injecting device is disclosed and can include a barrel, a plunger within the barrel, and a needle extending from the barrel. The needle can include a proximal end and a distal end. Further, a sensor can be incorporated in the needle substantially near the distal end of the needle.

In still another embodiment, a method of treating a patient is disclosed and can include placing a distal end of a cannulated sensing device on skin of the patient and receiving an indication from the cannulated sensing device that the cannulated sensing device is sensing subcutaneous fluid.

In yet still another embodiment, a kit is disclosed and can include an injecting device that can have a needle and a first sensor incorporated in the needle. Moreover, the kit can include a cannulated sensing device that can have a second sensor and a cannula. The cannula can receive the needle therethrough.

Description of a Cannulated Sensing Device

Referring to FIG. 1 through FIG. 4, a cannulated sensing device is shown and is generally designated 100. As shown, the cannulated sensing device 100 can include a housing 102 that can include a proximal end 104 and a distal end 106. The housing 102 can include a first portion 108 near the proximal end 104 of the housing 102. Further, the housing 102 can include a second portion 110 that extends from the first portion 108 and terminates at the distal end 106. In a particular embodiment, the first portion 108 of the housing 102 can be enlarged in order to accommodate one or more electronic components therein. For example, a battery and a microprocessor can be disposed within the first portion 108 of the housing.

FIG. 1 illustrates that a power switch 112 can be incorporated into, or extend through, the outer surface of the housing 102. For example, the power switch 112 can be incorporated in the second portion 110 of the housing 102 between the first portion 108 of the housing and the distal end 106 of the housing 102. More particularly, the power switch 112 can be incorporated into the second portion 110 of the housing 102 near, or adjacent to, the first portion 108 of the housing 102.

The cannulated sensing device 100 can also include a display device 114. The display device 114 can be a light emitting diode (LED), a liquid crystal display (LCD), or another display device. In a particular embodiment, the display device 114 can be incorporated into the outer surface of the housing 102. For example, the display device 114 can be incorporated into the second portion 110 of the housing 102 near, or adjacent to, the power switch 112. Further, in addition to, or in lieu of, the display device 114, the cannulated sensing device 100 can include an annunciator (not shown). The annunciator can emit a sound—e.g., a beep, a series of beeps, or a combination thereof.

Figure 2:
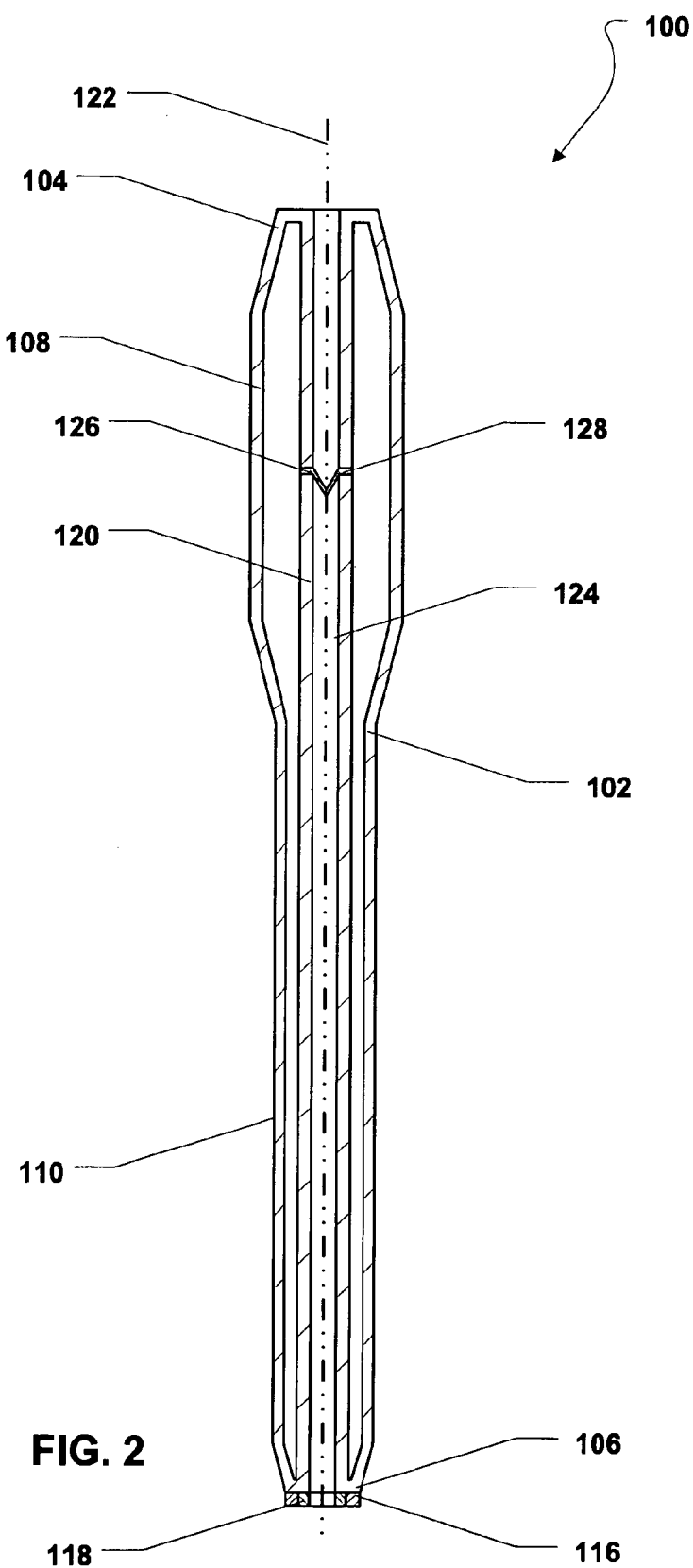
FIG. 2 is a cross-section view of the cannulated sensing device.

FIG. 1 and FIG. 2 further indicate that the cannulated sensing device 100 can include a sensor 116 that can be attached to, or otherwise extend from, the distal end 106 of the housing 102. Further, as shown in FIG. 2, the sensor 116 can surround a transmitter 118 that can also be attached to, or otherwise extend from, the distal end 106 of the housing 102. In a particular embodiment, the transmitter 118 can transmit a signal into a patient. The sensor 116 can sense at least a portion of the signal and a microprocessor (not shown) can use the signal to determine whether the cannulated sensing device 100 is over bone, flesh, or liquid.

In a particular embodiment, the display device 114 can provide a visual indication of the type of tissue that can be sensed by the cannulated sensing device 100. For example, the display device 114 can glow different colors or the display device 114 can flash with an increasing frequency based on the type of tissue or fluid that can be sensed by the cannulated sensing device 100. Further, the display device 114 can glow continuously when the cannulated sensing device 100 senses a particular tissue or fluid. For example, the display device 114 can glow continuously when the cannulated sensing device 100 senses a fluid.

Figure 3:
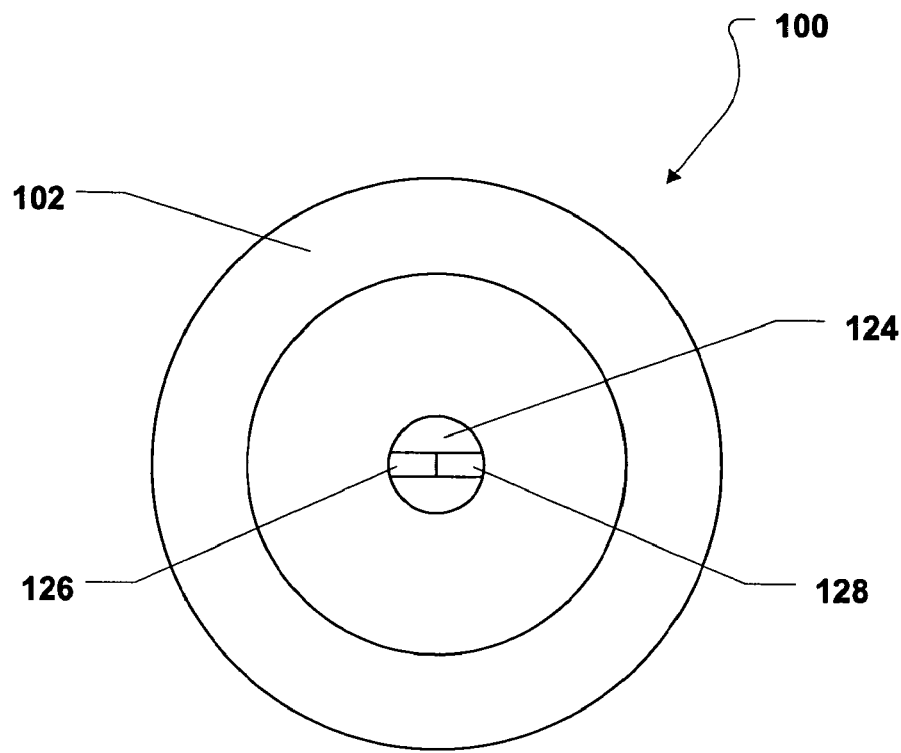
FIG. 3 is a proximal end view of the cannulated sensing device.
Figure 4:
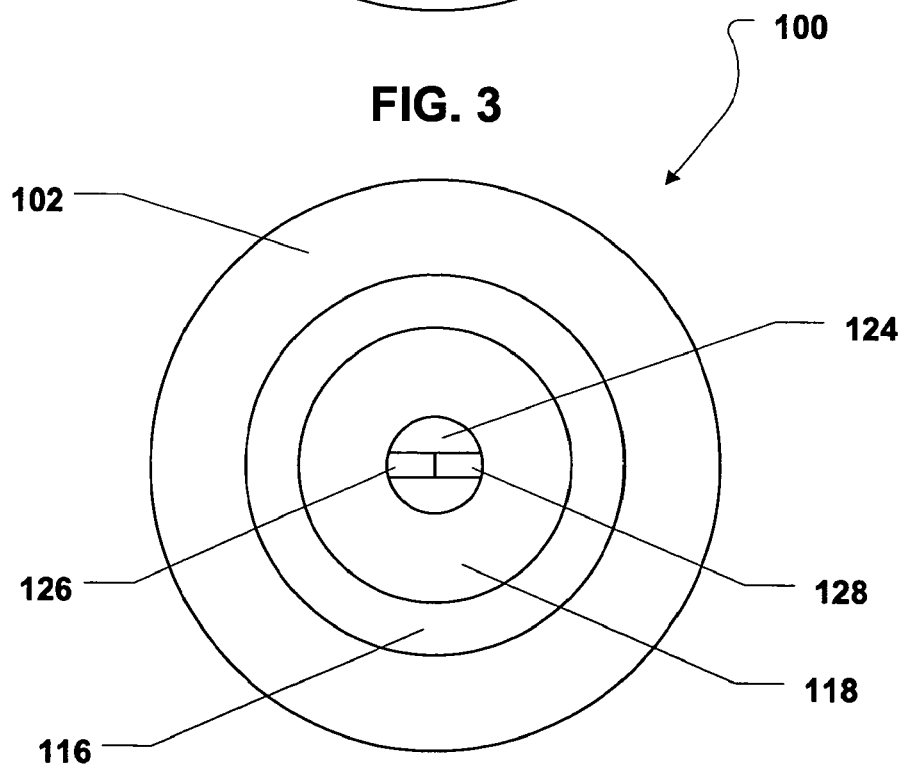
FIG. 4 is a distal end view of the cannulated sensing device.

FIG. 2 illustrates that the cannulated sensing device 100 can include a cannula 120 within the housing 102. The cannula 120 can extend from the proximal end 104 of the housing 102 to the distal end 106 of the housing 102 along a longitudinal axis 122. Further, the cannula 120 can include a lumen 124. As depicted in FIG. 2 through FIG. 4, a first spring loaded contact 126 and a second spring-loaded contact 128 can extend into the lumen 124 of the cannula 120. The spring-loaded contacts 126, 128 can be connected to the sensor 116. Alternatively, the spring-loaded contacts 126, 128 can be connected to a power source (not shown) and a microprocessor (now shown) within the cannulated sensing device 100.

Description of an Injecting Device

Figure 5:
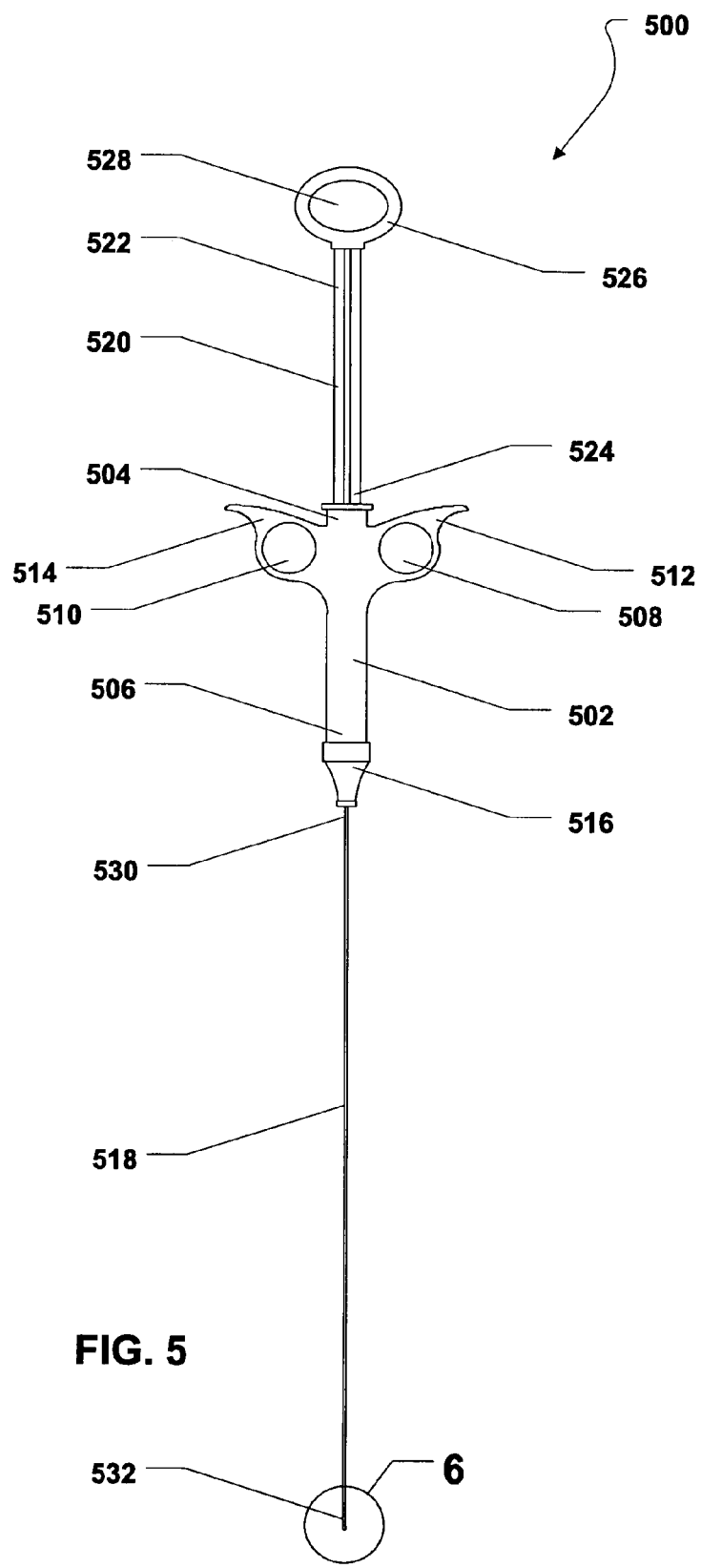
FIG. 5 is a plan view of an injecting device.

FIG. 5 illustrates an injecting device, generally designated 500, that can be used to deliver a therapeutic agent to an injection site. For example, the injecting device 500 can be used to deliver hyaluronic acid to synovial fluid within a synovial joint sack.

As shown in FIG. 5, the injecting device 500 can include a barrel 502 that can define a proximal end 504 and a distal end 506. The proximal end 504 of the barrel 502 of the injecting device 500 can include a first barrel handle 508 and a second barrel handle 510. The barrel handles 508, 510 can extend outward from the proximal end 504 of the barrel 502. The first barrel handle 508 can include a first finger hole 512 and the second barrel handle 510 can include a second finger hole 514. Each finger hole 512, 514 can be sized and shaped to receive a finger.

FIG. 5 indicates that the distal end 506 of the barrel 502 of the injecting device 500 can include a needle hilt 516. A needle 518 can be connected to and extend from the needle hilt 516.

As shown in FIG. 5, a plunger 520 can be disposed within the barrel 502 of the injecting device 500. The plunger 520 can include a proximal end 522 and a distal end 524. Also, the proximal end 522 of the plunger 520 can include a plunger handle 526 coupled thereto. The plunger handle 526 can include a thumb hole 528 that can be sized and shaped to receive a thumb. The plunger 520 can slide within the plunger barrel 502.

Figure 6:
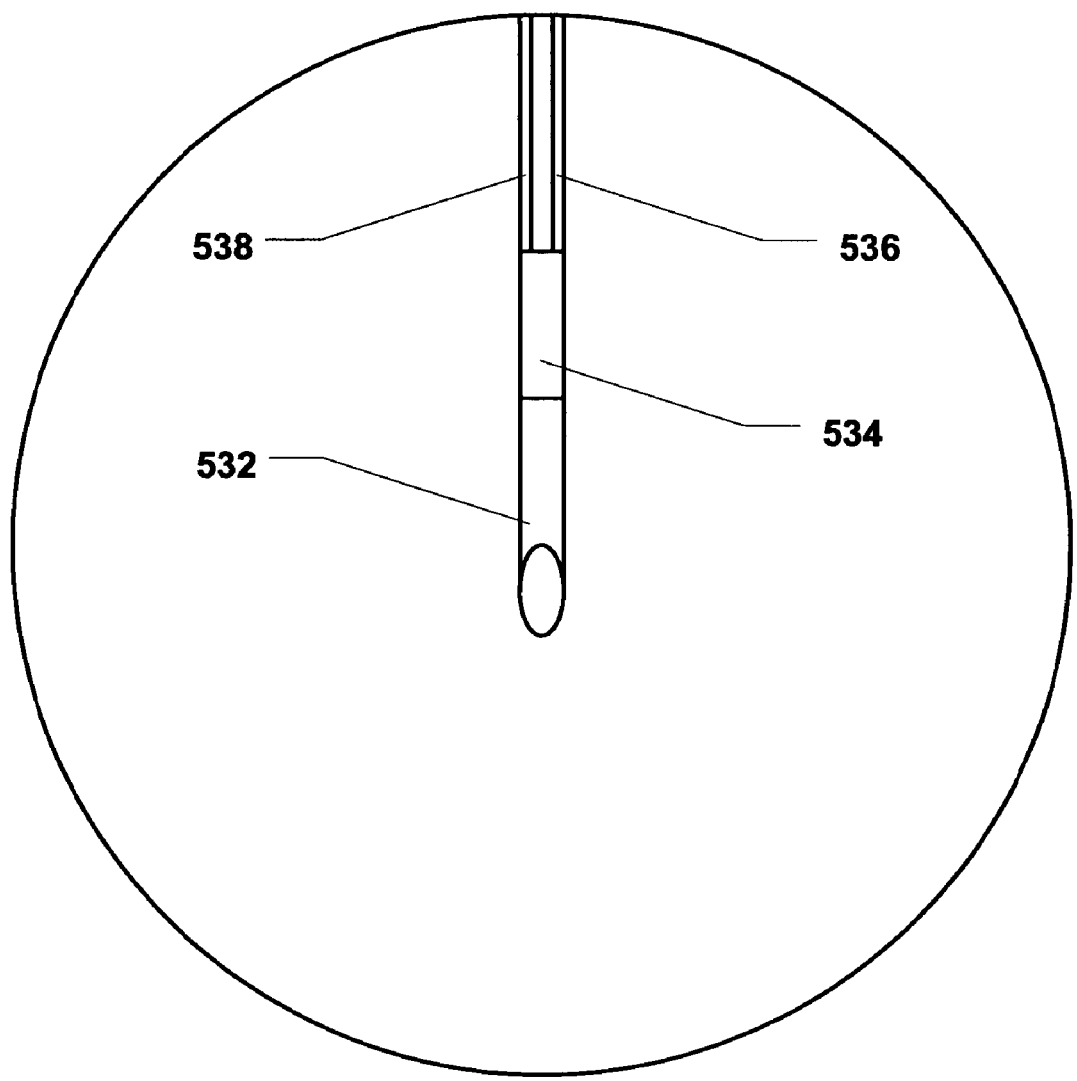
FIG. 6 is a detail view of the injecting device taken at circle 6 in FIG. 5.

Referring now to FIG. 6, the needle 518 can include a proximal end 530 and a distal end 532. Further, the needle can include a sensor 534 that can be slightly spaced from the distal end 532 of the needle 534. Moreover, a first conductor 536 and a second conductor 538 can lead from the sensor 534. Further, the first conductor 536 and the second conductor 538 can extend along the length of the needle 518 from the sensor 534 to the proximal end 530 of the needle 518.

In a particular embodiment, the injecting device 500 can be used in conjunction with a cannulated sensing device, e.g., the cannulated sensing device 100 described herein.

Description of the Cannulated Sensing Device Engaged with the Injecting Device

Figure 7:
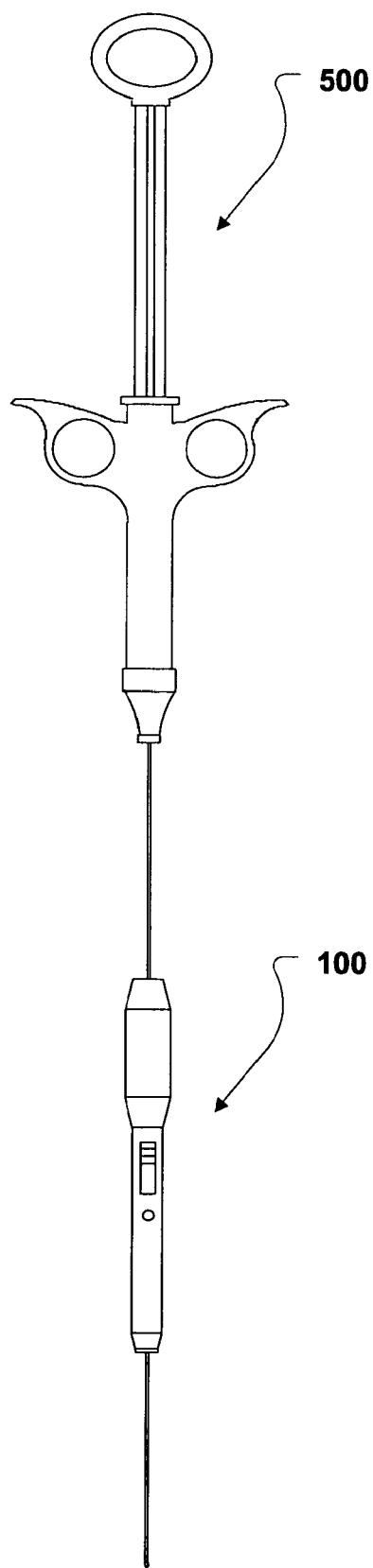
FIG. 7 is a first plan view of the injecting device inserted within the cannulated sensing device.
Figure 8:
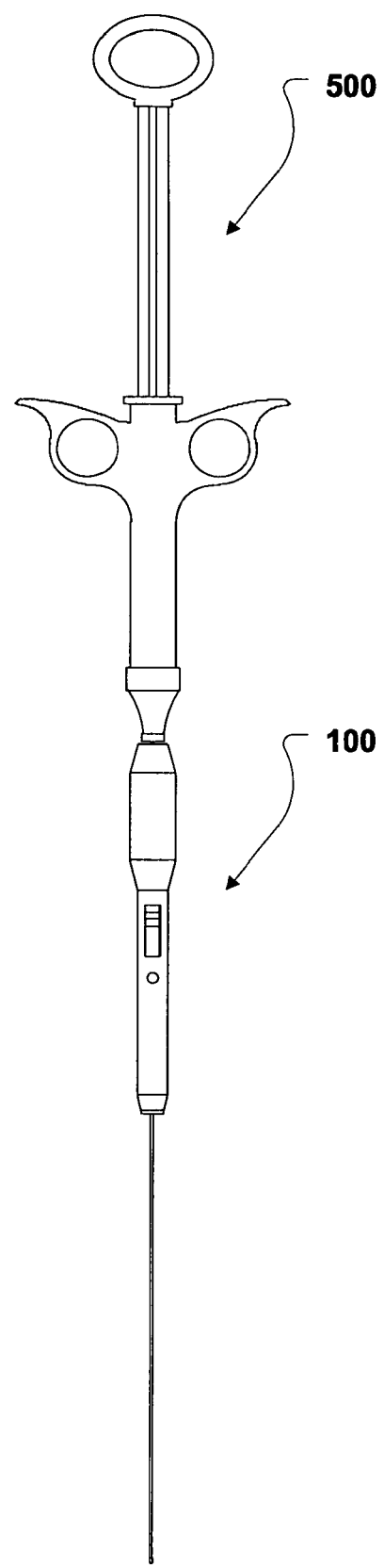
FIG. 8 is a second plan view of the injecting device inserted within the cannulated sensing device.

Referring now to FIG. 7 and FIG. 8, the injecting device 500 is shown installed within the cannulated sensing device 100. In particular, the needle 518 of the injecting device 500 can be installed within the lumen (not shown in FIG. 7 and FIG. 8) of the cannula (not shown in FIG. 7 and FIG. 8) of the cannulated sensing device 100. Further, the injecting device 500 can be moved linearly relative to the cannulated sensing device 100 such that a portion of the needle 518 extending beyond the distal end 106 of the cannulated sensing device 100 can increase in length. The injecting device 500 can move relative to the cannulated sensing device 100 until the proximal end 104 of the cannulated sensing device 100 contacts the needle hilt 516.

Accordingly, as described herein, the cannulated sensing device 100 can be placed against the skin of a patient and the needle 518 of the injecting device 500 can be moved through the cannulated sensing device 100 in order to inject a therapeutic agent in a patient at a location aligned with the cannulated sensing device 100 along a patient's skin.

In a particular embodiment, as the injecting device 500 is slid into the cannulated sensing device 100, the needle 518 extending from the injecting device 500 can contact at least one of the spring loaded contacts 126, 128 and extend the reach of the sensor 116. In other words, the needle 518, or the sensor 534 incorporated into the needle 518, can become part of the sensor 116 in the cannulated sensing device 100.

Alternatively, the sensor 534 incorporated into the needle 518 can become electrically connected to a microprocessor and a power source within the cannulated sensor 100 via the spring-loaded contacts 126, 128. Further, the sensor 534 within the needle 518 can temporarily replace the sensor 116 within the cannulated sensing device 100.

For example, the spring-loaded contacts 126, 128 can complete a portion of a circuit including the sensor 116 within the cannulated sensing device 100 when the spring-loaded contacts 126, 128 are in contact with each other. However, when the needle 518 is placed within the cannulated sensing device 100, the needle 518 can separate the spring-loaded contacts 126, 128 and break a portion of a circuit that can include the sensor 116 within the cannulated sensing device 100. Further, one or more of the conductors 536, 538 along the length of the needle 518 can contact the spring loaded contacts 126, 128.

Accordingly, the sensor 116 within the cannulated sensing device 100 can be deactivated, or de-energized, by separating the spring-loaded contacts 126, 128 from each other. Further, the sensor 534 within the needle 518 can be activated, or energized, when the conductors 536, 538 along the length of the needle 518 contact the spring-loaded contacts 126, 128. Thereafter, the sensor 534 within the needle 518 can sense signals from the transmitter 118 within the cannulated sensing device 100 and send data back to the microprocessor within the cannulated sensing device 100 in order to determine a location of the distal end 532 of the needle 518 relative to bone, flesh, fluid, or a combination thereof.

Description of the Electronic Components of the Cannulated Sensing Device

Figure 9:
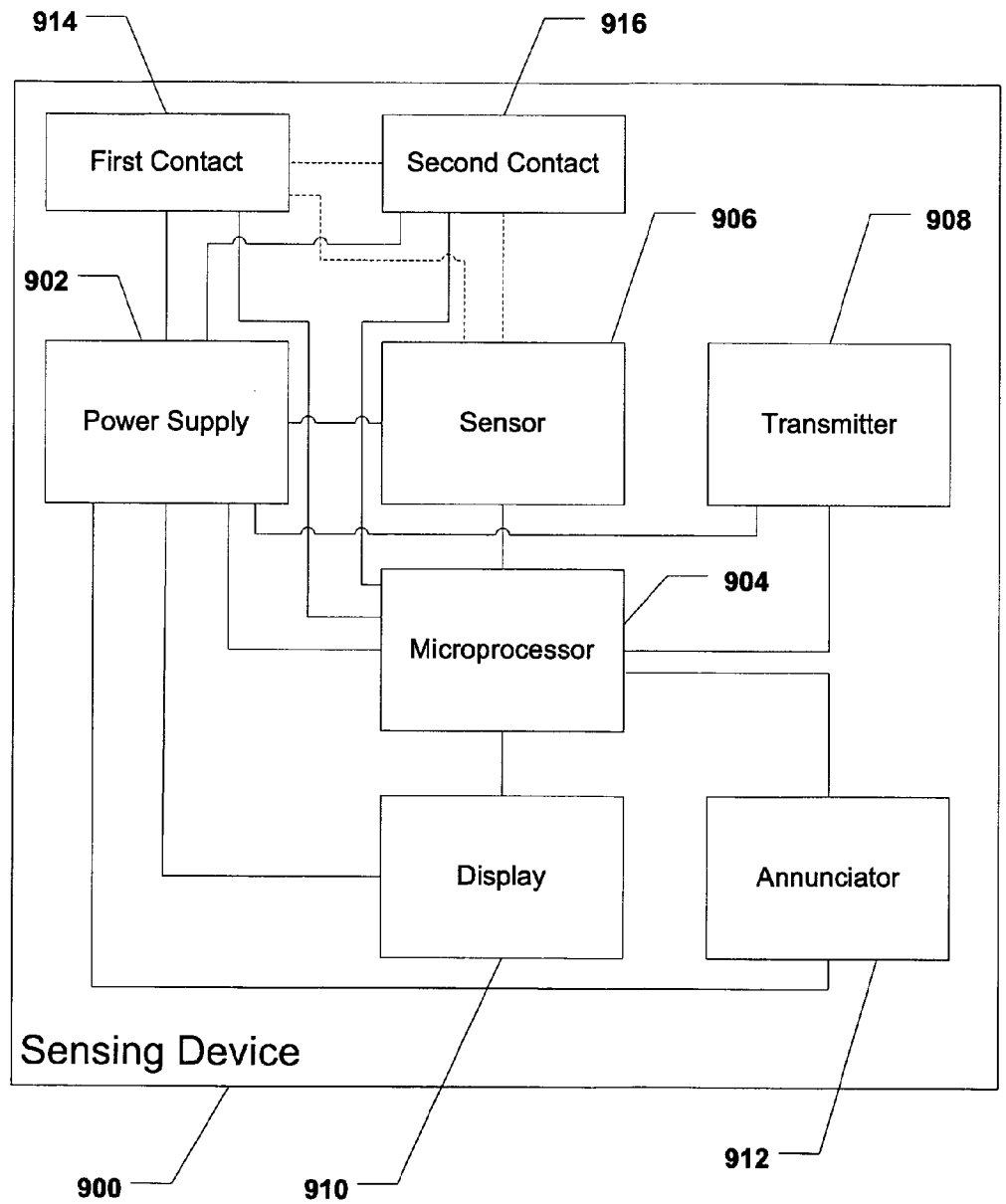
FIG. 9 is a block diagram representing the electronic components within the cannulated sensing device.

FIG. 9 is a block diagram that illustrates the electronic components within the cannulated sensing device, generally designated 900. As shown, the cannulated sensing device 900 can include a power supply 902. A microprocessor 904 can be electrically connected to the power supply 902. Further, a sensor 906 can be electrically connected to the power supply 902 and can be placed in communication with the microprocessor 904. Moreover, a transmitter 908 can be electrically connected to the power supply 902 and can be placed in communication with the microprocessor 904.

As shown in FIG. 9, a display 910 can be electrically connected to the power supply 902 and can be placed in communication with the microprocessor 904. Also, an annunciator 912 can be electrically connected to the power supply 902 and can be placed in communication with the microprocessor 904. Further, as indicated in FIG. 9, a first contact 914 and a second contact 916 can be electrically connected to the power supply 902 and the microprocessor 904. In addition, or alternatively, the first contact 914 and the second contact 916 can be electrically connected to the sensor 906.

In a particular embodiment, placed "in communication with" can mean physically connected via a wire or other conductor. "In communication with" can also mean connected in any manner that facilitates transfer of a desired signal or information, such as via a wireless connection, e.g., an infrared (IR) connection, a radio frequency (RF) connection, a Wi-Fi connection, a Bluetooth connection, etc. Further, in a particular embodiment, the display 910 can be a display device such as, a liquid crystal display (LCD), a light emitting diode (LED), etc. Also, in a particular embodiment, the annunciator 912 can be a sound emitting device, such as a device that emits a beep, a series of beeps, or a combination thereof.

Description of a Method of Treating a Patient

Figure 10:
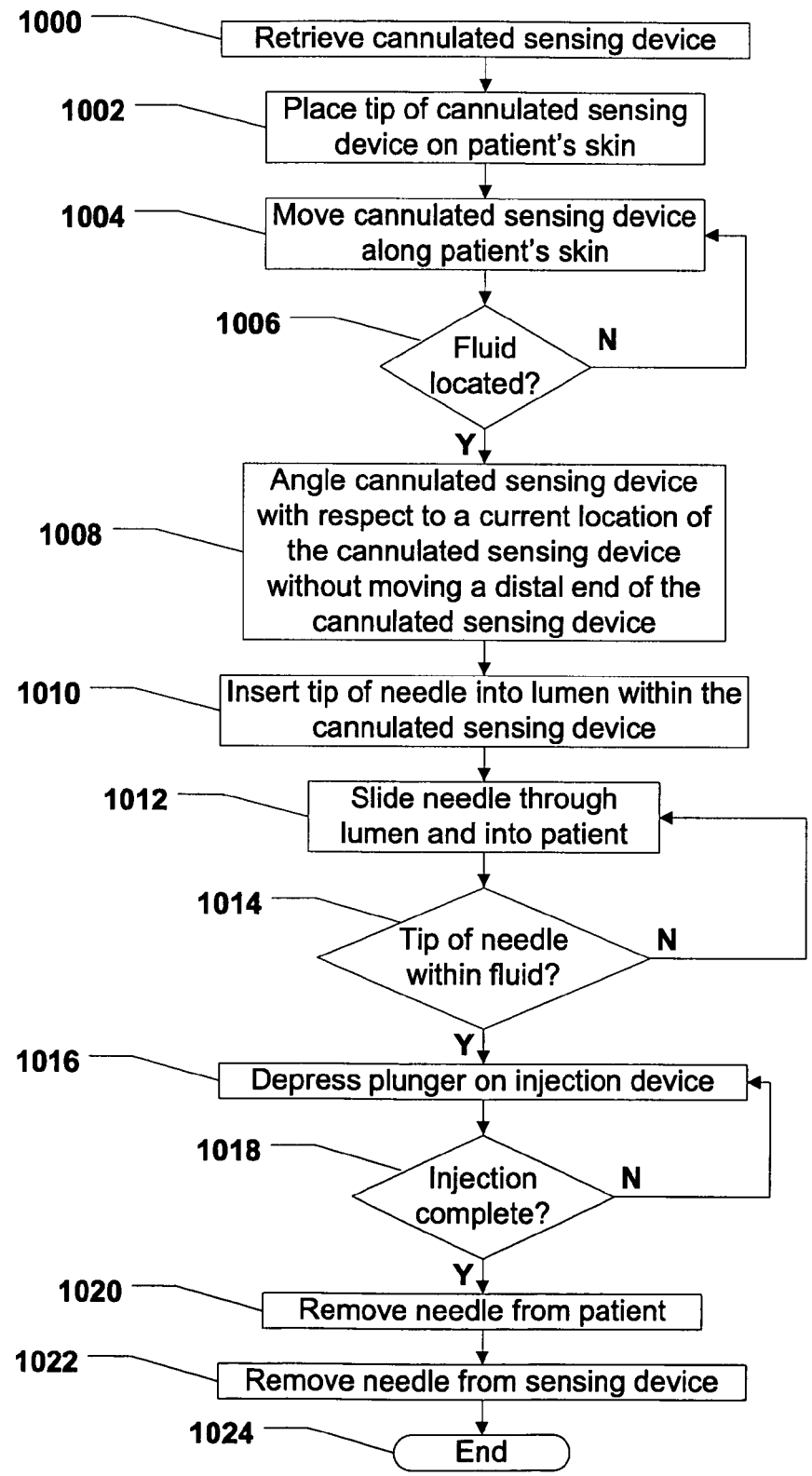
FIG. 10 is a flow chart illustrating a method of treating a patient.

Referring now to FIG. 10, a method of treating a patient is shown and commences at block 1000. Commencing at block 1000, a cannulated sensing device can be retrieved. At block 1002, a tip of the cannulated sensing device can be placed on patient's skin. Thereafter, at block 1004, the cannulated sensing device can be moved along the patient's skin. Moving to block 1006, it can be determined whether subcutaneous fluid, such as synovial fluid, is located beneath the sensing device. In a particular embodiment, the cannulated sensing device can be used to determine whether subcutaneous fluid is located thereunder. Further, an LED on the cannulated sensing device can notify a user when subcutaneous fluid is located. The cannulated sensing can distinguish among hard tissue (e.g., bone), soft tissue (e.g., flesh or muscle), and fluid (e.g., synovial fluid). For example, the cannulated sensing device can make these distinctions using ultrasound signals or other acoustic signals. Further, the cannulated sensing device can transmit an electrical signal and measure an impedance of the electrical signal in order to distinguish hard tissue, soft tissue, and fluid.

If fluid is not located, the method can return to block 1004 and a user can continue to move the sensing device along the patient's skin. If fluid is located, the method can move to block 1008. At block 1008, the cannulated sensing device can be angled, if necessary, with respect to the current location of the tip of the cannulated sensing device without moving the tip.

Proceeding to block 1010, a tip of a needle of an injecting device can be inserted into a lumen within the cannulated sensing device. Thereafter, at block 1012, the needle can be slid, or otherwise moved, through the lumen and into a patient. At block 1014, it can be determined whether the tip of the needle is within fluid, e.g., within synovial fluid, within the patient. In a particular embodiment, the needle itself can extend the sensing capability of a sensor within the cannulated sensing device and can be used, in conjunction with the cannulated sensing device, in order to determine whether the tip of the needle is within fluid. Further, the LED of the cannulated sensing device can indicate to the user when the tip of the needle is indeed located in fluid within the patient.

If the needle is not within fluid within the patient, the method can return to block 1012 and the user can continue to slide, or otherwise move, the needle of the injecting device through the lumen of the cannulated sensing device. Conversely, if the tip of the needle is within fluid within the patient, the method can continue to block 1016 and a plunger on the injecting device can be depressed, i.e., slid into the injecting device, in order to inject a therapeutic agent, such as hyaluronic acid, into the patient.

Continuing to decision step 1018, it can be determined whether injection is complete. This determination can be made based on one or more gradations on the injecting device that can indicate an amount of a therapeutic agent injected from the injecting device. If the injection is not complete, the method can return to 1016 and the plunger can be moved further into the injecting device in order to expel more therapeutic agent from the injecting device.

On the other hand, at decision step 1018, if injection is complete, the method can proceed to block 1020. At block 1020, the needle of the injecting device can be removed, or otherwise withdrawn, from the patient. At block 1022, the needle of the injecting device can be removed, or otherwise withdrawn, from the cannulated sensing device. The method can then end at state 1024.

CONCLUSION

With the configuration of structure described above, the cannulated sensing device provides a device that can be used to distinguish hard tissue, soft tissue, and fluid. Further, the cannulated sensing device provides a device that can be used to locate fluid, e.g., synovial fluid, prior to injecting a therapeutic agent into the fluid. Moreover, the cannulated sensing device provides a device that can be used to position a distal end, or tip, of a needle prior to injecting a therapeutic agent into a patient using the needle.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A cannulated sensing device, comprising:
    a housing having an axis, a proximal end and a distal end;
    a cannula having a lumen extending axially from the proximal end of the housing to the distal end of the housing, and the lumen is configured to receive a needle of an injecting device;
    a circuit extending into the lumen to couple with the needle;
    a sensor attached to the distal end of the housing to sense hard tissue, soft tissue, fluid, or a combination thereof axially beyond the distal end of the housing, and an axial reach of the sensor is extended when the needle couples with the circuit;
    a microprocessor in communication with the sensor.

2. The cannulated sensing device of claim 1, further comprising a power supply connected to the microprocessor and the sensor.

3. The cannulated sensing device of claim 2, further comprising a transmitter attached to the distal end of the housing, wherein the transmitter is in communication with the microprocessor.

4. The cannulated sensing device of claim 2, further comprising a power switch coupled to the power supply.

5. The cannulated sensing device of claim 2, wherein the microprocessor and the power supply are a located within the housing.

6. The cannulated sensing device of claim 1, further comprising a display device configured to indicate whether the cannulated sensing device senses hard tissue, soft tissue, fluid, or a combination thereof.

7. The cannulated sensing device of claim 6, wherein the sensor and the display device are incorporated into the housing.

8. The cannulated sensing device of claim 1, further comprising an annunciator configured to indicate whether the cannulated sensing device senses hard tissue, soft tissue, fluid, or a combination thereof.

9. The cannulated sensing device of claim 1, wherein the sensor is activated when the needle is inserted within the cannula of the cannulated sensing device.

10. The cannulated sensing device of claim 9, wherein the sensor is deactivated when the needle is withdrawn from the cannula of the cannulated sensing device.

11. The cannulated sensing device of claim 9, further comprising a needle sensor on the needle adjacent a distal end of the needle, a first conductor extending substantially along a length of the needle from the needle sensor to the proximal end of the needle.

12. The cannulated sensing device of claim 11, further comprising a second conductor extending substantially along the length of the needle from the needle sensor to the proximal end of the needle.

* * * * *